(12) United States Patent
Stutz et al.

(10) Patent No.: US 8,378,140 B2
(45) Date of Patent: Feb. 19, 2013

(54) PROCESSES FOR PREPARING LOW-CHLORINE ISOCYANATES

(75) Inventors: Herbert Stutz, Dormagen (DE); Frank Diehl, Leichlingen (DE); Alexander Schwarz, Leverkusen (DE); Rainer Bruns, Leverkusen (DE)

(73) Assignee: Bayer MaterialScience AG, Leverkusen (DE)

( * ) Notice: Subject to any disclaimer, the term of this patent is extended or adjusted under 35 U.S.C. 154(b) by 1064 days.

(21) Appl. No.: 12/195,495

(22) Filed: Aug. 21, 2008

(65) Prior Publication Data
US 2009/0054684 A1      Feb. 26, 2009

(30) Foreign Application Priority Data
Aug. 22, 2007   (EP) .................................... 07016422

(51) Int. Cl.
*C07C 263/00*      (2006.01)
(52) U.S. Cl. ...................................................... 560/347
(58) Field of Classification Search .................. None
See application file for complete search history.

(56) References Cited

U.S. PATENT DOCUMENTS

| 3,331,873 A | 7/1967 | De Long et al. |
| 4,764,308 A | 8/1988 | Sauer et al. |
| 4,847,408 A | 7/1989 | Frosch et al. |
| 6,800,781 B2 | 10/2004 | Herold et al. |
| 2006/0047170 A1 | 3/2006 | Keggenhoff et al. |
| 2006/0099138 A1 | 5/2006 | Walsdorff et al. |
| 2009/0149671 A1* | 6/2009 | Stutz et al. .................... 560/347 |

FOREIGN PATENT DOCUMENTS

| EP | 0289840 | 11/1988 |
| EP | 1403248 | 3/2004 |
| EP | 1640341 | 3/2006 |
| WO | WO-97/24320 | 7/1997 |
| WO | WO-2004/037718 | 5/2004 |

* cited by examiner

*Primary Examiner* — Yevegeny Valenrod
(74) *Attorney, Agent, or Firm* — Connolly Bove Lodge & Hutz LLP

(57) ABSTRACT

Processes comprising providing an amine reactant, and reacting the amine reactant with a stream of phosgene in a reaction zone to form a product comprising a corresponding isocyanate, wherein the phosgene stream has a CO content of 0.5% by weight or more.

20 Claims, No Drawings

PROCESSES FOR PREPARING LOW-CHLORINE ISOCYANATES

BACKGROUND OF THE INVENTION

The phosgenation of aliphatic or aromatic amines for the preparation of isocyanates can be carried out with particular advantage in the gas phase. Such processes are well established in principle in the art, such as described in European Patent Publication No. FP 0289840, the entire contents of which are incorporated herein by reference, and such processes have since become established industrially.

International Patent Publication No. WO 97/24320, the entire contents of which are incorporated herein by reference, generally describes a process for producing isocyanates by reacting the corresponding (aromatic) amines with phosgene using recycled chlorine, in which process phosgene produced from specially purified chlorine from a special electrochemical cell and a non-specifically defined carbon monoxide excess is passed directly into a phosgeniation reactor. No concentration data are provided. No description is provided of the starting products or of the resulting secondary components in the phosgene or of the effect on the quality of the isocyanates produced. Nor are any details provided of the phosgenation process, whether it is conducted with or without a solvent, or of the temperature range over which the isocyanate production is carried out.

Phosgenation on the industrial scale is typically carried out using phosgene prepared in a phosgene generator over a catalyst of chlorine and carbon monoxide. Before being supplied to the phosgenation, the phosgene from the generator is first supplied to a purifying stage where it is separated into a waste gas stream and a phosgene stream, preferably by condensing out phosgene or by distillation. Prior to the actual reaction with the amine, the phosgene stream is then also usually mixed with recycled phosgene, such as disclosed in International Patent Publication No. WO 2004/037718, the entire contents of which are incorporated herein by reference.

Phosgene used in accordance with the prior art possesses residual CO gas levels, owing to the aftertreatment steps, of less than 0.05% by weight.

Following the reaction of amine and phosgene, the resultant isocyanate is purified conventionally by distillation to remove low-boiling and high-boiling by-products. In many instances it is problematic if the purified isocyanates are coloured or if subsequent modification steps such as the prepolymerization, biuretization or trimerization, for example, are accompanied by unwanted side reactions which again, ultimately, impact adversely on the colouring of the polyisocyanates obtained.

Side reactions of this kind are often triggered by very low concentrations of compounds which are chlorinated or include chlorine in a hydrolyzable form. In principle it is possible to remove those compounds which contribute to the hydrolyzable chlorine content (HC compounds and HC content) or to the total chlorine content of the isocyanates, but from a production standpoint it is undesirable to do so, since an additional purifying step of this kind increases the production costs through an increased use of energy and/or loss of yield owing to thermal loading.

BRIEF SUMMARY OF THE INVENTION

The present invention relates generally to processes for preparing isocyanates which feature a particularly low level of compounds that comprise chlorine in optionally hydrolyzable form.

The present invention provides processes which, as compared with processes of the prior art, lead to products having significantly reduced HC and total chlorine contents, without further purification steps.

Surprisingly, it has now been found that a reduction in the levels of compounds which contribute to the HC content and to the total chlorine content can be achieved if the phosgene supplied to the amine phosgenation has a carbon monoxide (CO) content of 0.5% by weight or more.

The present invention accordingly provides for the use of phosgene having a carbon monoxide content of 0.5% by weight or more for the phosgenation of amines.

The invention further provides a process for preparing isocyanates by reaction of the corresponding amines with phosgene, optionally in the presence of an inert medium, wherein the phosgene stream supplied to the phosgenation has a CO content of 0.5% by weight or more.

One embodiment of the present invention includes processes comprising: providing an amine reactant; and reacting the amine reactant with a stream of phosgene in a reaction zone to form a product comprising a corresponding isocyanate; wherein the phosgene stream has a CO content of 0.5% by weight or more.

DETAILED DESCRIPTION OF THE INVENTION

As used herein, the singular terms "a" and "the" are synonymous and used interchangeably with "one or more" and "at least one," unless the language and/or context clearly indicates otherwise. Accordingly, for example, reference to "a stream" herein or in the appended claims can refer to a single stream or more than one stream.

Preferably the phosgene stream has a CO content of more than 1% by weight, more preferably more than 2% by weight. The CO content of the phosgene, however, is preferably below 8% by weight, very preferably below 4% by weight. Thus, in various preferred embodiments, the phosgene stream has a CO content of 1 to 8% by weight, 2 to 8% by weight, 1 to 4% by weight, and 2 to 4% by weight.

With regard to the provision of the CO content in the phosgene, it is immaterial whether the CO is supplied separately to the phosgene or whether a phosgene stream obtained from the phosgene production process and already containing CO in the as-claimed range is used as a source of phosgene for the phosgenation of the invention.

Preferably the mixture of CO and phosgene obtained directly from the phosgene generator is supplied to the phosgenation without further working-up and depletion of CO.

A preferred process for phosgene generation includes the preparation of phosgene from chlorine and carbon monoxide as described in U.S. Patent Application Publication No. US 2006/047170, the entire contents of which are incorporated herein by reference, in the presence of an activated-carbon catalyst in a tube-bundle reactor, with efficient cooling, with gas temperatures of below 100° C. Another feature of such preferred processes for the generation of phosgene is that the removal of the heat of reaction by evaporative cooling with water at reduced pressure takes place below the atmospheric pressure of 1 bar absolute. The coolant circuit is a closed circuit in which water is evaporated, diverted, condensed elsewhere and then passed back for renewed evaporation to the coolant chamber. This coolant chamber preferably contains liquid water in the boiling state at all times. The CO and chlorine feedstock streams are used in the preferred process, for the purpose of achieving a low level of chlorine in the phosgene, preferably in a molar CO excess of 2% to 20%, more preferably 5% to 15%.

The phosgene stream supplied to the reaction zone for reaction with an amine reactant preferably has an HCl content of less than 15% by weight, more preferably of 0.1% to 10% by weight, very preferably 2% to 8% by weight.

Processes for preparing isocyanates in accordance with the various embodiments of the present invention are preferably carried out in one stage. This means that the mixing and reaction of the reactants to form the product takes place in one reaction zone. After the products have left the reaction zone, the reaction of the supplied amino groups with phosgene is preferably complete. One particular reason why this is a worthwhile aim is because, otherwise, unreacted amino groups can lead to the formation of hydrochloride or urea, which reduces the total isocyanate yield and, as a result of the formation of deposits, reduces the service life of the reactor and/or the service life of the downstream work-up apparatus.

Preference is likewise given to continuous operation of the processes of the invention.

For the processes of the invention it is possible to use all amino-functional compounds having at least one, preferably 1 to 3, primary amino groups, provided that they can be converted into the vapor form. In this context it is immaterial whether the amines are aliphatic, cycloaliphatic, araliphatic or aromatic in nature.

Aforementioned amino-functional compounds typically have up to 22 carbon atoms; if there are two or more amino groups in the molecule, they are separated from one another by at least 2 carbon atoms.

It is preferred to use amines of the aforementioned type which can be converted into the gas phase without substantial decomposition.

Particularly suitable for this purpose are diamines based on aliphatic or cycloaliphatic hydrocarbons having 2 to 18 carbon atoms.

Examples of such include 1,4-diaminobutane, 1,6-diaminohexane, 1,8-diaminooctane, 1,10-diaminodecane, 1,6-diamino-2,4,4-trimethylhexane and 1,6-diamino-2,2,4-trimethylhexane, 1-amino-3,3,5-trimethyl-5-aminomethylcyclohexane (IPDA), 2,4-, or 2,6-diamino-1-methylcyclohexane and 4,4'- and/or 4,2'-diaminodicyclohexylmethane. Particularly preferred are 1,6-diaminohexane, 1-amino-3,3,5-trimethyl-5-(aminomethyl)cyclohexane, and 4,4'- and/or 4,2'-di(aminocyclohexyl)methane.

Likewise suitable as amine reactants are any desired (cyclo)aliphatic triamines having up to 22 carbon atoms, provided that they are stable under the temperature conditions of the process of the invention and can be converted into the vapor form. They may be, for example, triaminocyclohexane, tris(aminomethyl)cyclohexane, triaminomethylcyclohexane. Likewise suitable are 1,8-diamino-4-(aminomethyl)octane, 1,6,11-undecanetriamine, 1,7-diamino-4-(3-amino-propyl)heptane, 1,6-diamino-3-(aminomethyl)hexane or 1,3,5-tris(aminomethyl)cyclohexane.

For the process of the invention it is likewise possible to use aromatic amines which preferably can be converted into the gas phase without substantial decomposition. Examples of preferred aromatic amines are tolylenediamine (TDA), as the 2,4 or 2,6 isomer or as a mixture thereof, diaminobenzene, 2,6-xylidine, naphthylenediamine (NDA) and 2,4'- or 4,4'-methylene(diphenylamine) (MDA) or isomer mixtures thereof. Preference is given to 2,4- and/or 2,6-TDA.

The amine and phosgene reactants can each also be metered into the reaction chamber together with an inert medium. The inert medium comprises a medium which at the reaction temperature is in gas form in the reaction chamber and does not react with the compounds which occur in the course of reaction. The inert medium is generally mixed with amine and/or phosgene prior to the reaction, but may also be metered in separately from the reactant streams. By way of example it is possible to use nitrogen, noble gases, such as helium or argon, or aromatics, such as chlorobenzene, dichlorobenzene, xylene or carbon dioxide. Preference is given to using nitrogen and/or chlorobenzene and/or dichlorobenzene as an inert medium.

The inert medium is generally used in an amount such that the ratio of gas volume of the inert medium to gas volume of the amine or phosgene is 0.001 to 5, preferably 0.01 to 3, more preferably 0.1 to 1. Preferably the inert medium is introduced together with the amines into the reaction chamber.

The processes of the invention are preferably carried out in such a way that the amine and phosgene reactants and also the isocyanate formed in the reaction zone are in the gaseous state under the reaction conditions; in other words, such that the formation of drops of liquid is preferentially ruled out.

For the provision of the aforementioned reaction conditions, the temperatures in the reaction zone are preferably more than 200° C., more preferably more than 260° C., very particularly more than 280° C. The upper temperature limit in this case is preferably below 570° C., more preferably below 500° C.

The reaction of phosgene with amine in the respective reaction zone takes place at absolute pressures of more than 0.1 bar to less than 20 bar, preferably 0.5 bar to 10 bar, more preferably 0.7 bar to 5 bar, very preferably 0.8 to 3 bar.

The pressure in the feed lines to the reaction zone is generally higher than the above-indicated pressure in the reaction zone itself. The pressure in the feed lines is preferably 20 to 2000 mbar, more preferably from 30 to 1000 mbar, higher than in the reaction zone itself.

In general the pressure in the regions of the process that follow the reaction zone proper is lower than in the reaction zones themselves. The pressure there is preferably lower by 10 to 500 mbar, more preferably 30 to 150 mbar, than in the reaction zone.

The reactants are preferably passed into and through the reaction zone at a linear flow rate of 1 to 100 m/s in each case, more preferably of 2 to 50 m/s.

The flow rates of the two reactants within the aforementioned regions are preferably adjusted such that the average contact time of the reaction mixture of amines and phosgene that is attained in the reaction zone is generally from 0.01 second to less than 15 seconds, preferably from more than 0.04 second to less than 10 seconds, more preferably from more than 0.08 second to less than 5 seconds. By average contact time is meant the period from the beginning of the mixing of the reactants until the departure from the reaction chamber to the work-up stage. In one preferred embodiment the flow in the process of the invention is characterized by a Bodenstein number of more than 10, preferably more than 100 and more preferably of more than 250.

The dimensions of the reaction chamber and the flow rates are advantageously chosen such that the prevailing flow is turbulent, i.e. is a flow having a Reynolds number of at least 2300, preferably at least 2700, for the reaction mixture, the Reynolds number being formed with the hydraulic diameter of the reaction chamber.

As a result of the turbulent flow a narrow residence time with a small standard deviation of below 10% is achieved, preferably below 6%.

The reaction zone preferably possesses no moveable internals.

The reaction zone can be temperature-controlled via its exterior surface. In order to construct production units with a high capacity it is possible for two or more reactor tubes to be connected in parallel. Alternatively the reaction can take place preferably adiabatically. This means that flows of heating or cooling energy do not flow with technical measures over the exterior surface of the reaction volume. Preferably the reaction takes place adiabatically.

When the reaction mixture has been reacted in the reaction zone, it is necessary to cool the reaction gases rapidly after the phosgenation reaction to temperatures below 180° C. in order to avoid the formation of unwanted by-products as a result of the thermal breakdown of di-/triisocyanate or as a result of a continuing reaction, by polymerization, since the di-/triisocyanates formed are not thermally stable at the reaction temperatures of 300 to 570° C. Cooling to temperatures of 100 to 180° C. takes place in a single-stage or multi-stage scrubber (quench with scrubbing column) using an inert solvent, as described in EP-A1 1403248, column 2, line 39-column 3, line 18.

Suitable solvents are preferably hydrocarbons, substituted where appropriate by halogen atoms, such as, for example, chlorobenzene, dichlorobenzene, and toluene. Solvents employed with particular preference are monochlorobenzene and/or dichlorobenzene. As a solvent it is possible to use the isocyanate or a solution of the prepared isocyanate in the stated solvents, and this solution can also be circulated via a heat exchanger for the removal of energy. At the scrubbing stage, the isocyanate is transferred selectively into the scrubbing solution. From the isocyanate-free gas which remains (excess phosgene, hydrogen chloride, the inert medium if appropriate, and solvent from the scrubber) the solvent is recovered by partial condensation and then the phosgene is recovered, by means for example of absorption in monochlorobenzene and/or dichlorobenzene, and the hydrogen chloride, following purification where appropriate, is put to further use as a raw material in accordance with the prior art. The concentrated isocyanate solution obtained in the quench and scrubbing column has an isocyanate concentration of at least 20% by weight, preferably of at least 25% by weight. The concentrated isocyanate solution obtained in the quench and scrubbing column is freed from physically (dissolved) and chemically attached hydrogen chloride and phosgene, preferably by means of rectification, and in further distillation stages is separated into pure solvent, low-boiling by-products, pure di- or triisocyanate, and high boilers. Preference is given to using the isocyanate.

The amounts of compounds with hydrolyzable chlorine possessed by the (cyclo)aliphatic isocyanates obtainable by the processes of the invention are preferably less than 200 ppm, more preferably less than 80 ppm.

The amounts of compounds with hydrolyzable chlorine possessed by the aromatic isocyanates obtainable by the processes of the invention are preferably less than 100 ppm, more preferably less than 40 ppm.

The total chlorine content in the case of the (cyclo)aliphatic and in the case of the aromatic isocyanates is preferably below 800 ppm, more preferably below 500 ppm.

The determination of the amount of hydrolyzable chlorine in isocyanates in the working range w(Cl)>5 mg/kg is accomplished by urethanization, hydrolysis and potentiometric titration with silver nitrate, using a combined silver/silver chloride electrode.

To determine the hydrolyzable chlorine content, the isocyanate sample is admixed with methanol and urethanized under reflux for 10 minutes. Subsequently, following dilution with water, the mixture is hydrolysed by boiling under reflux. The ionogenic chlorine formed in this procedure is acidified with nitric acid, made up with a known mass of sodium chloride, and then subjected to argentometric titration against a silver nitrate standard solution. The titration is carried out with incremental reagent metering and with automatic endpoint evaluation under drift control (equilibrium titration). The initial mass of the isocyanate sample and the consumption of silver nitrate standard solution are used to calculate the hydrolysable chlorine content, with account being taken of the make-up material.

The isocyanates obtainable by the process of the invention can be used with particular advantage in the production of polyurethane coating materials and also adhesives and sealants and both flexible and hard foams. For these purposes they are preferably first reacted to form prepolymers, uretdiones, isocyanurates, iminooxadiazinediones, biurets or allophanates, and may also be blocked by methods that are typical per se in the art.

The invention will now be described in further detail with reference to the following non-limiting examples.

EXAMPLES

Example 1

Comparative Example

Supplied continuously to a tube reactor with downstream isocyanate condensation stage and a subsequent distillative isocyanate work-up stage, by mixing in a smooth-jet nozzle, were reactant stream A, an isophoronediamine/inert gas mixture, and reactant stream B, phosgene obtained by evaporating a solution of phosgene (recovered excess) in monochlorobenzene and by evaporating condensed phosgene from the phosgene generation process, the quantity introduced being 160% of theory. The gaseous phosgene stream contained 2.9% by weight hydrogen chloride and >0.05% by weight carbon monoxide. The temperatures of the two reactant streams were 300° C. The pressure in the tube reactor was slightly above atmospheric pressure, at 1300 mbar.

The rate of component A in the smooth-jet nozzle was approximately 80 m/s, that of component B prior to mixing approximately 10 m/s. As a result of the adiabatic reaction regime, the temperature in the reactor rose to approximately 420° C.

After leaving the reactor, the isophorone diisocyanate (IPDI) reaction product was condensed, separated from the hydrogen chloride by-product, the inert substances and the excess phosgene, and then purified in the distillation sequence. The IPDI obtained had a hydrolysable chlorine content of 140 ppm and a total chlorine content of 190 ppm.

The resultant IPDI was processed further to form the trimer, a trifunctional polyisocyanate with a very low vapour pressure that is employed in coating systems. In solution at 70% in a commercially customary paint solvent, the trimer was virtually water-clear with a Hazen colour number of 50 Apha.

Example 2

Inventive

Example 1 was repeated under the same conditions, the phosgene reactant stream B was again 160% of theory, recovered to an extent of 60% by evaporating a solution of recycled phosgene, and the phosgene needed for the reaction was supplied directly from the phosgene generation process, in gas form, including the inert substances and the excess carbon monoxide. The gaseous phosgene stream prior to entry into the reactor contained 3.1% by weight hydrogen chloride and 2.3% by weight carbon monoxide.

The IPDI obtained from the distillation sequence had a hydrolysable chlorine content of 80 ppm and a total chlorine content of 100 ppm.

The resultant IPDI was likewise processed further to form the trimer. In solution at 70% in a commercially customary paint solvent, the trimer was virtually water-clear, with a Hazen colour number of 30 Apha.

Example 3

Comparative Example

Supplied continuously to a tube reactor with downstream isocyanate condensation stage and distillative isocyanate work-up stage following it, by mixing in a smooth-jet nozzle, were reactant stream A, hexamethylenediamine/inert gas mixture, and reactant stream B, phosgene obtained by evaporating a solution of phosgene (recovered excess and condensed phosgene from the phosgene generation process) in monochlorobenzene, the quantity introduced being 220% of theory. The phosgene reactant stream B contained 6.9% by weight hydrogen chloride and >0.05% by weight carbon monoxide. The temperatures of the two reactant streams were 300° C. The pressure in the tube reactor is slightly above atmospheric pressure, at 1400 mbar.

The rate of component A in the smooth-jet nozzle was approximately 50 m/s, that of component B prior to mixing approximately 10 m/s. As a result of the adiabatic reaction regime, the temperature in the reactor rose to approximately 450° C.

After leaving the reactor, the hexamethylene diisocyanate (HDI) reaction product was condensed, separated from the hydrogen chloride by-product, the inert substances and the excess phosgene, and then purified in the distillation sequence. The HDI obtained had a hydrolysable chlorine content of 50 ppm and a total chlorine content of 430 ppm.

The resultant HDI was processed further to form the trimer, a trifluctional polyisocyanate with a very low vapour pressure that is employed in coating systems. The trimer was virtually water-clear, with a Hazen colour number of 80 Apha.

Example 4

Inventive

Example 3 was repeated under the same conditions, the phosgene reactant stream B was again 220% of theory, recovered to an extent of 120% by evaporating a solution of recycled phosgene, and the phosgene needed for the reaction was supplied directly from the phosgene generation process, including the inert substances and the carbon monoxide. The phosgene reactant stream B contained 6.3% by weight hydrogen chloride and 3.4% by weight carbon monoxide.

The HDI obtained from the distillation sequence had a hydrolysable chlorine content of 20 ppm and a total chlorine content of 190 ppm.

The resultant HDI was likewise processed farther to form the trimer. The trimer was virtually water-clear, with a Hazen colour number of 20 Apha.

Example 5

Inventive

Supplied to a tube reactor with downstream isocyanate condensation stage and distillative isocyanate work-up stage following it, by mixing in a nozzle, are reactant stream A, a mixture consisting of gaseous 2,4- and 2,6-tolylenediamine and also inert gas, and reactant stream B, phosgene 75% by evaporation of a solution of phosgene (recovered excess), and the phosgene needed for the reaction, directly from the phosgene generation process, in gas form, including the inert substances and the excess carbon monoxide. The gaseous phosgene stream from the phosgene generation process contained 5.0% carbon monoxide.

The pressure in the tube reactor is slightly above the atmospheric pressure, at 1500 mbar. As a result of the adiabatic reaction regime, the temperature in the reactor rose to approximately 450° C.

The reaction product, as a mixture consisting of 2,4- and 2,6-tolylene diisocyanate (TDI), was condensed after leaving the reactor, separated from the by-product hydrogen chloride, the inert substances and the excess phosgene, and then purified in the distillation sequence. The resulting TDI had a hydrolysable chlorine content of 30 ppm and a total chlorine content of 80 ppm, with a Hazen colour number of 20 Apha.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process comprising: providing an amine reactant; and reacting the amine reactant with a stream of phosgene in a reaction zone to form a product comprising a corresponding isocyanate; wherein the phosgene stream has a CO content of 0.5% by weight or more.

2. The process according to claim 1, wherein reacting the amine reactant with the stream of phosgene is carried out such that formation of droplets in the reaction zone is excluded.

3. The process according to claim 1, wherein the phosgene stream has a CO content of 1% by weight or more.

4. The process according to claim 1, wherein the phosgene stream has a CO content of less than 8% by weight.

5. The process according to claim 1, wherein the phosgene stream has a CO content of 1 to 8% by weight.

6. The process according to claim 1, wherein the phosgene stream has an HCl content of 0.1% to 10% by weight.

7. The process according to claim 1, wherein reacting the amine reactant with the stream of phosgene is carried out in the presence of an inert medium comprising one or more components selected from the group consisting of nitrogen, chlorobenzene, dichlorobenzene and mixtures thereof.

8. The process according to claim 5, wherein reacting the amine reactant with the stream of phosgene is carried out in the presence of an inert medium comprising one or more components selected from the group consisting of nitrogen, chlorobenzene, dichlorobenzene and mixtures thereof.

9. The process according to claim 1, wherein reacting the amine reactant with the stream of phosgene is carried out in the reaction zone at a temperature of 200 to 570° C. and an absolute pressure of 0.8 to 3 bar.

10. The process according to claim 8, wherein reacting the amine reactant with the stream of phosgene is carried out in the reaction zone at a temperature of 200 to 570° C. and an absolute pressure of 0.8 to 3 bar.

11. The process according to claim 9, wherein pressure in one or both of a feedline for the amine reactant and a feedline for the stream of phosgene is 20 to 2000 mbar greater than the pressure in the reaction zone, and wherein pressure downstream of the reaction zone is 10 to 500 mbar less than the pressure in the reaction zone.

12. The process according to claim 1, wherein the amine reactant and the stream of phosgene each independently have a linear flow rate into and through the reaction zone of 1 to 100 m/s, and wherein amine reactant and the stream of phosgene have an average contact time with each other in the reaction zone of 0.01 to 15 seconds.

13. The process according to claim 11, wherein the amine reactant and the stream of phosgene each independently have a linear flow rate into and through the reaction zone of 1 to 100 m/s, and wherein amine reactant and the stream of phosgene have an average contact time with each other in the reaction zone of 0.01 to 15 seconds.

14. The process according to claim 1, wherein reacting the amine reactant with the stream of phosgene is carried out adiabatically.

15. The process according to claim 1, wherein the corresponding isocyanate comprises an aliphatic or cycloaliphatic isocyanate comprising less than 200 ppm of compounds having hydrolyzable chlorine.

16. The process according to claim 1, wherein the corresponding isocyanate comprises an aromatic isocyanate comprising less than 100 ppm of compounds having hydrolyzable chlorine.

17. The process according to claim 1, wherein the stream of phosgene is supplied to the process directly from a phosgene generation process without intervening purification.

18. The process according to claim 17, wherein the phosgene generation process comprises a reaction of CO and chlorine with a molar excess of the CO over the chlorine of 2 to 20%.

19. The process according to claim 17, further comprising recovering unreacted phosgene from the reaction of the amine reactant and the stream of phosgene, and mixing the recovered phosgene with the phosgene supplied directly from a phosgene generation process before the stream of phosgene enters the reaction zone.

20. The process according to claim 18, further comprising recovering unreacted phosgene from the reaction of the amine reactant and the stream of phosgene, and mixing the recovered phosgene with the phosgene supplied directly from a phosgene generation process before the stream of phosgene enters the reaction zone.

* * * * *